United States Patent [19]

Mellor et al.

[11] 4,038,863

[45] Aug. 2, 1977

[54] MACHINE FOR TESTING AND COMPARING BEARINGS AND BEARING MATERIALS

[75] Inventors: Harrison Clay Mellor, Newtown Square; Lawrence A. Peacock, Norristown, both of Pa.

[73] Assignee: Arguto, Inc., Aston, Pa.

[21] Appl. No.: 743,505

[22] Filed: Nov. 19, 1976

[51] Int. Cl.² ............................................. G01N 19/02
[52] U.S. Cl. ........................................................ 73/9
[58] Field of Search .......................................... 73/9, 7

[56] References Cited

U.S. PATENT DOCUMENTS

| 3,040,560 | 6/1962 | Stupp | 73/9 |
| 3,271,995 | 9/1966 | Bäumler | 73/9 |

FOREIGN PATENT DOCUMENTS

| 156,732 | 8/1963 | U.S.S.R. | 73/9 |

OTHER PUBLICATIONS

"True Life" Testing Cues Bearing Designs, in Research/Development, pp. 12-14, Feb. 1960.

Primary Examiner—Richard C. Queisser
Assistant Examiner—Joseph W. Roskos
Attorney, Agent, or Firm—Howson and Howson

[57] ABSTRACT

A machine for testing and comparing bearings of the plain or sliding type and bearing materials comprising one or a pair of bearing test stations each having a test bearing housing for fixedly retaining a selected test bearing. A rotatably driven shaft is journalled in the test bearing. Means are provided for applying a predetermined load radially on the test bearing in the housing and means are also provided for measuring the friction force generated by rotation of the shaft in the test bearing, whereby the coefficient of friction of the test bearing can be determined. Means are also provided for damping oscillations occurring in the test bearing housing and for limiting rotation of the test bearing and housing under excess generated friction force.

22 Claims, 6 Drawing Figures

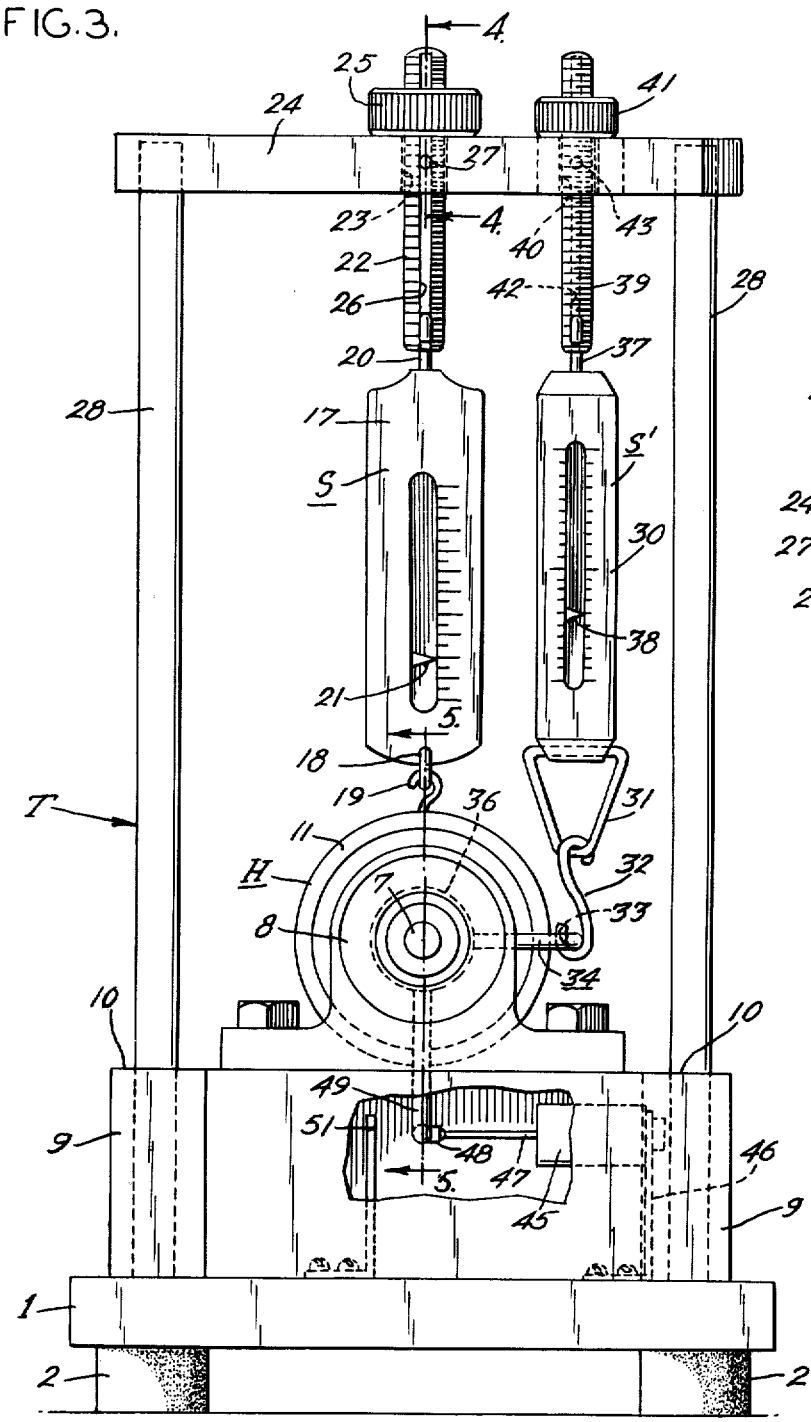
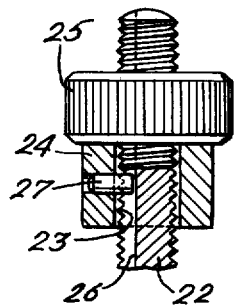
FIG.3.
FIG.4.

MACHINE FOR TESTING AND COMPARING BEARINGS AND BEARING MATERIALS

This invention relates to new and useful improvements in machines for testing and comparing bearings and bearing materials. More particularly the invention relates to a machine for testing and comparing relatively small so-called plain or sliding bearings of the oilless or self-lubricating type such as bearings of plastic or impregnated wood, sintered metals and the like.

Sliding bearings are bearings other than ball, roller and needle bearings, wherein the interface movement consists of one surface sliding over another, such as in journal or sleeve bearings on a shaft. Load and speed are the two primary factors in selecting a sliding bearing for a particular application. Loads for sliding bearings are computed on the basis of pounds per inch of the projected area of the bearing which is the product of the inside diameter of the bearing and the length of said bearing. Journal velocities in sliding bearings are normally measured in feet per minute at the interface between the sliding surfaces which is the product of the shaft circumference in inches and the revolutions per minute of said shaft divided by 12.

For sliding bearings operating under conditions of boundary lubrication or dry lubrication there is a direct relationship between the speed and load that can be carried by any bearing material. The greater the load the less allowable speed and conversely the greater the speed the less the allowable load. The relationship between the load carrying capacity of the bearing and the sliding velocity with bearings operating in the range of boundary lubrication is customarily expressed as the PV factor of the bearing and rated accordingly. The PV factor is the unit load P in pounds per square inch of the projected area of the bearing and the sliding velocity V in feet per minute. The $PV$ factor for any given sliding bearing is determined by the following formula:

$$PV = \frac{W}{L} \times \frac{\pi n}{12} \text{ or } \frac{.2618 \, W n}{L}$$

wherein $W$ is the total load in pounds, $L$ is bearing length in inches and $n$ is the sliding interface velocity in revolutions per minute. For example, a sliding bearing having a length of 1 inch and an internal diameter of $\frac{1}{2}$ inch under a total load of 20 pounds at a sliding velocity of 1725 rpm, has a PV factor of about 9000.

Also, the rotation of a shaft in a plain sliding bearing generates a friction force at the bearing — shaft interface that acts in the direction of rotation of the shaft. The amount of this generated friction force depends upon the value of the coefficient of friction of the bearing and the bearing load on the shaft. Accordingly, with a known radial load W applied to a bearing, if the generated friction force F is measured, the coefficient of friction of the test bearing can be readily determined by the following formula:

$$C_f = \frac{F \text{ (lbs)}}{W \text{ (lbs)}}$$

The coefficient of friction of a test bearing is an important factor as it bears directly on the energy consumption and heat generation rates of the bearing and can be used to predict the wear characteristics of the bearing. In the case of viscous lubricated bearings, such as oil impregnated wood and sintered metal bearings, the coefficient of friction also indicates the quality of the lubricant film.

With the foregoing in mind, an object of the present invention is to provide a machine of the character described that is capable of performing functional and comparative tests on full scale radially loaded plain sliding bearings.

Another object of the invention is to provide a machine as described that is operable to test two sliding bearings simultaneously under similar conditions so that direct performance comparison can be made between various selected bearings.

Another object of the invention is to provide a machine as set forth that is operable for performing endurance and life tests on plain sliding bearings at predetermined PV values and to accurately measure and determine the dynamic coefficient of friction of such bearings under any given load and speed at all times during the test period.

A further object of the invention is to provide a machine embodying the foregoing objectives that is comparatively inexpensive to manufacture, is of compact, lightweight, portable construction, and is relatively easy to operate.

These and other objects of the invention and the various features thereof, as well as the construction and operation of a typical embodiment of the invention, are hereinafter set forth and described with reference to the accompanying drawings in which:

FIG. 3 is an elevational view in enlarged scale on line 3—3 of FIG. 2;

FIG. 4 is an enlarged fragmentary sectional view on line 4—4 of FIG. 3;

Figure 1:
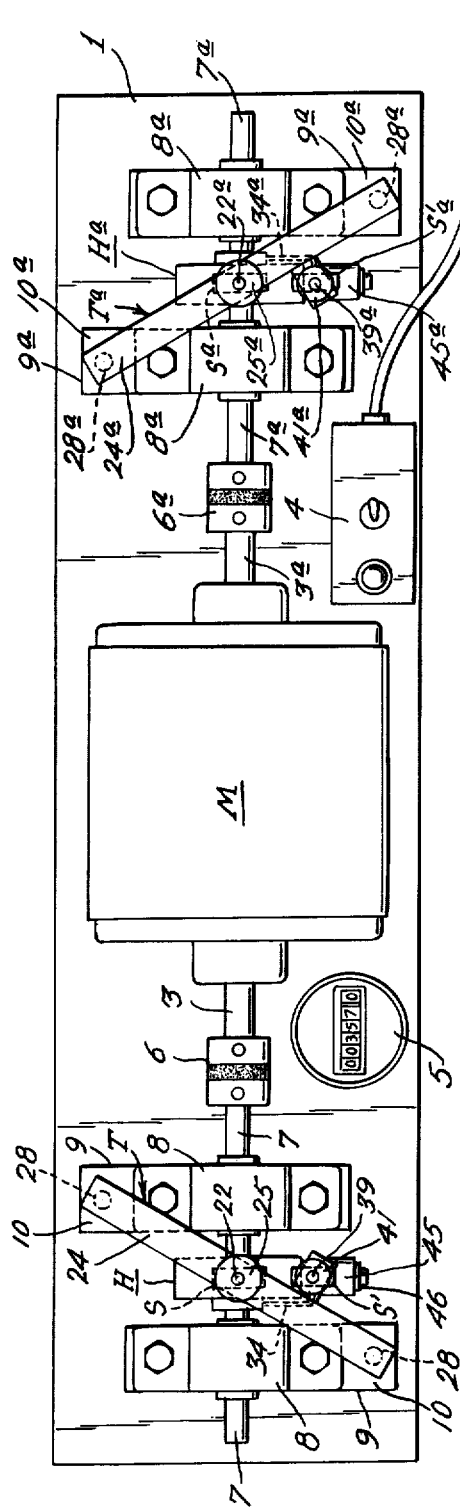
FIG. 1 is a plan view of one embodiment of a machine made in accordance with the present invention for testing and comparing bearings and bearing materials.
Figure 2:
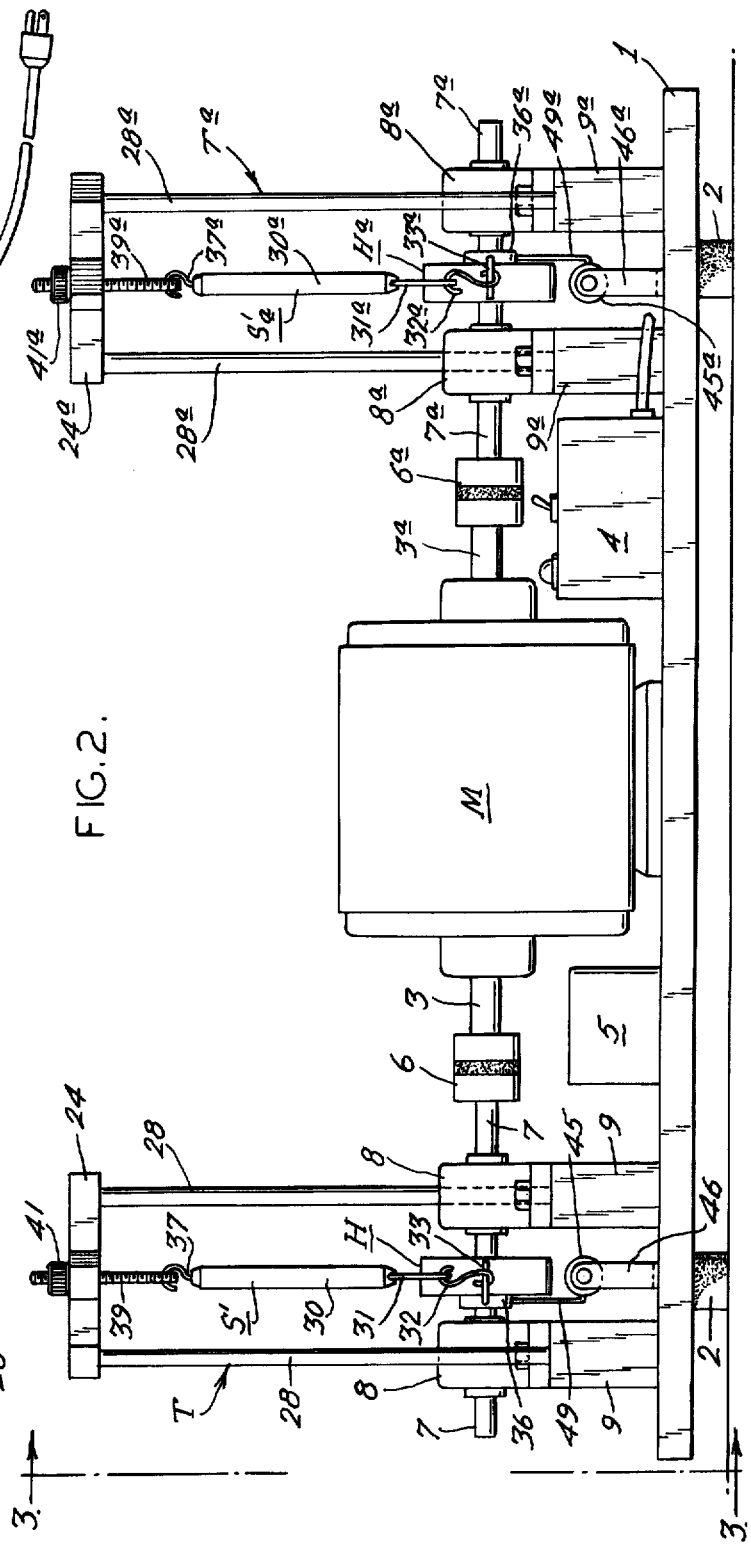
FIG. 2 is a front elevational view of the invention disclosed in FIG. 1.

Referring now to the drawings, and particularly FIGS. 1 and 2 thereof, the machine embodiment disclosed comprises a rectangular flat base 1 having a plurality of supporting legs 2 of suitable resilient material such as rubber or the like. Mounted centrally on the upper surface of the base 1 is a constant speed electrical motor M having oppositely extending coaxial shafts 3 and 3a respectively. Preferably the motor M is of the capacitor-start, induction-run having high starting torque and high break-down torque operable on conventional 115 volt, single phase, 60 cycle current. The motor M is also equipped with a built-in thermal overload protection of the manual reset type.

Operation of the motor M is controlled by a 2-pole manual starter switch 4 mounted on the base 1 adjacent said motor and this switch is also equipped with a manual reset thermal overload protector having high sensitivity and operable to effect rapid shut-off of the motor in the event of overload due to high friction or seizure of one or both of the bearings being tested in the machine as hereinafter set forth. An elapsed-time hour meter 5 that indicates tenths of hours up to 99,999.9 hours is mounted on the base 1 and wired in parallel with the motor M so that said hour meter will run when the motor M is running.

Connected coaxially to each motor shaft 3 and 3a, respectively, through a conventional coupling 6 and 6a, is a test bearing shaft 7 and 7a. Each shaft 7 and 7a is rotatably mounted in a pair of aligned axially spaced conventional pillow block bearings 8 and 8a, respectively. The pair of pillow block bearings 8 and 8a are bolted to underlying supports 9 and 9a that are fixedly secured upon the upper surface of the machine base 1. The supports 9 for the pillow block bearings 8 and the supports 9a for the pillow block bearings 8a are transversely offset relative to each other as shown in FIG. 1 of the drawings so that they extend laterally beyond one side of each pillow block bearing and provide flat mounting surfaces 10 and 10a for bearing test structures hereinafter described.

Figure 5:
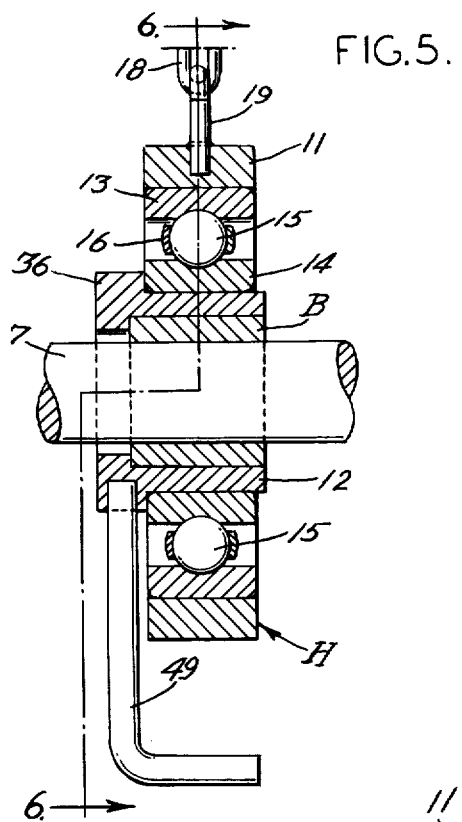
FIG. 5 is an enlarged fragmentary sectional view on line 5—5 of FIG. 3.

Associated with each shaft 7 and 7a driven by the motor M is a bearing test structure generally designated T and Ta, respectively. Since both of these test structures are identical, only the test structure T will be described in detail and corresponding parts in the other test structure Ta are indicated in the drawings by the same reference numbers followed by the letter a. Accordingly, in the test bearing structure T associated with the shaft 7 to the left of the motor M in FIGS. 1 and 2 of the drawings, there is provided an annular bearing housing H comprising a continuous outer ring 11 and a continuous inner ring 12 fabricated of bearing steel. As shown in FIG. 5 the outer and inner rings 11 and 12 of the housing H are of relatively short axial length dimensioned to be received freely between the axially spaced pillow block bearings 8 in which the shaft 7 is journalled. Interposed between the outer and inner rings 11 and 12 of the housing H is a conventional ball bearing assembly comprising outer race 13, inner race 14 and an intermediate series of bearing balls 15 and cage 16.

In accordance with the present invention the outer race 13 of the ball bearing assembly is fixedly secured within the outer ring 11 of the housing H against relative rotation with respect thereto and in similar manner the inner race 14 of the bearing assembly is fixedly secured within the inner ring 12 of the test bearing housing H. A test bearing B, i.e., the bearing to be tested, is fabricated from a selected bearing material and dimensioned to provide an internal diameter to fit on the shaft 7 and an external diameter relative to the inner housing ring 12 such that the test bearing B can be press-fitted within said inner ring 12 and secured therein against rotation relative to said ring 12.

The housing H with the test bearing B fixedly secured therein as described is mounted on the shaft 7 intermediate the axially spaced pillow blocks 8, 8 substantially as shown in FIGS. 1 and 2 of the drawings. In accordance with the invention, for test purposes a variable radial load is applied to the outer ring 11 of the housing H. In the illustrated embodiment of the invention the radial load is applied to the test bearing by means of a spring scale S disposed in vertical position above the housing H so that the load of the spring scale S is applied radially to the housing in the vertical plane containing the common axis of the housing H, test bearing B and shaft 7. Thus, as shown in FIG. 3 of the drawings, the lower end of the housing 17 of the spring scale S has a depending eye or loop 18 through which is connected hook 19 that is fixedly secured to the housing outer ring 11 in the vertical plane containing the common axis of the housing H, test bearing B and shaft 7 as aforesaid.

The vertically movable arm 20 of the load scale S with its indicating pointer 21, has it upper end connected to the lower end of a vertically extending threaded rod 22. The upper portion of the threaded rod 22 projects through a bore 23 in a crosshead 24 and a knurled hand nut 25 is threaded on the rod 22 into abutting contact with the upper surface of the crosshead 24. As shown in FIGS. 3 and 4, the threaded rod 22 is provided at one side thereof with a longitudinally extending groove or key way 26 that slidably receives therein a key or pin 27 mounted in the crosshead 24 to thereby prevent rotation of the threaded rod 22 relative to said crosshead while permitting vertical movement of said rod 22 relative to the crosshead 24.

The crosshead 24 is supported horizontally in a fixed elevated position above and angularly crosswise of the shaft 7 by means of a pair of rigid vertical posts 28. The upper ends of the posts 28 are secured respectively adjacent opposite ends of the crosshead 24 and the lower ends of said posts are fixedly mounted on the flat supporting surface portions 10, 10 of the pillow block supports 9, 9. By reason of the construction described, it will be apparent that by turning the hand nut 25 in the appropriate direction on the threaded rod 22 the spring tension in the scale S and therefore the radial load applied to the test bearing, may be increased or decreased as desired.

As previously described, rotation of the shaft 7 in the test bearing B generates a friction force that acts in the direction of rotation of said shaft 7, and since the coefficient of friction in any given case is equal to the generated friction force divided by the applied radial load, it is necessary to measure the friction force generated at any given load in order to determine the coefficient of friction of the test bearing.

Figure 6:
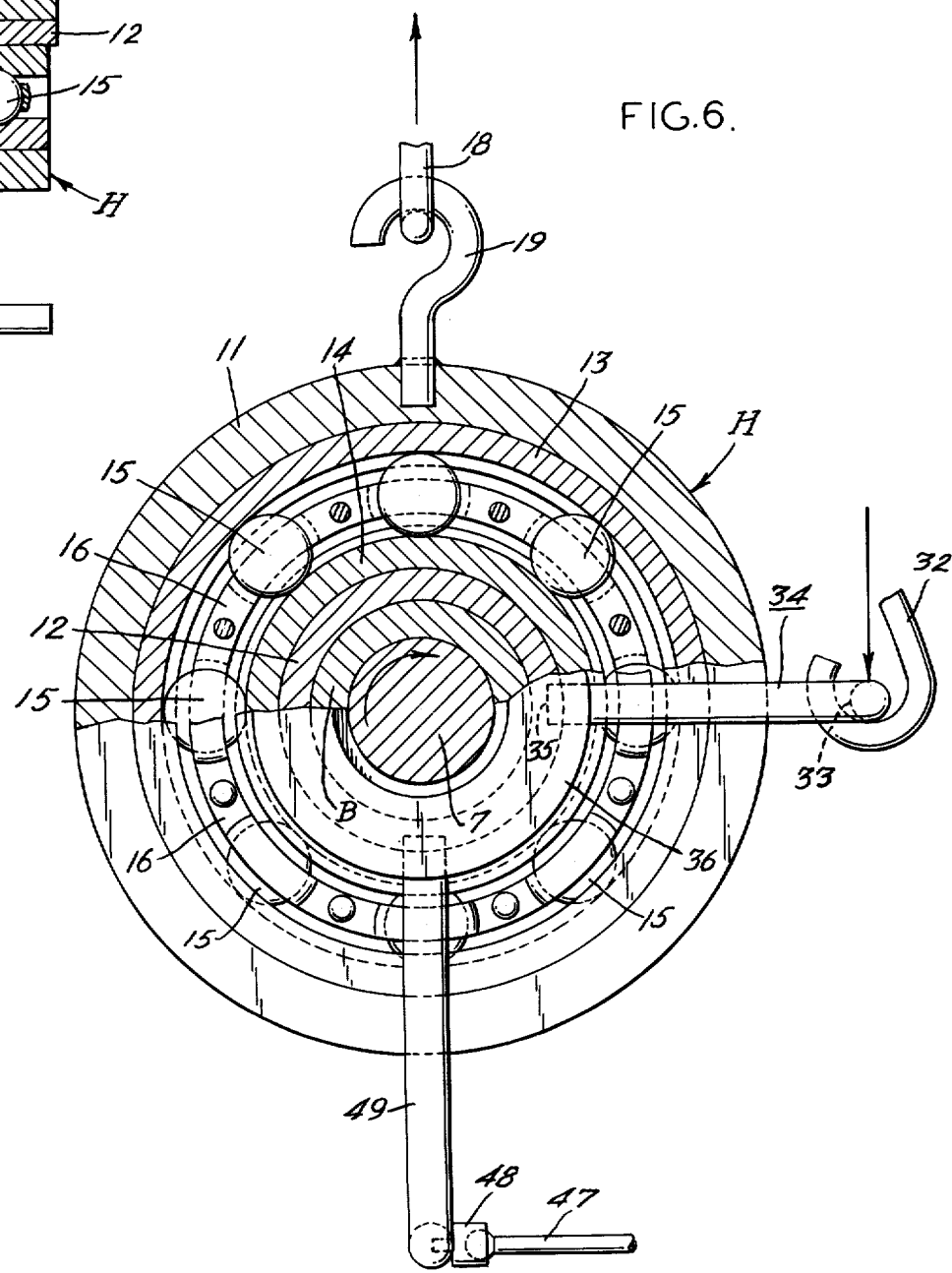
FIG. 6 is an enlarged fragmentary view partially in section on line 6—6 of FIG. 5.

In the illustrated embodiment of the invention the generated friction force is measured and determined by means of a second spring scale S' that is vertically disposed parallel to the load scale S and connected between the crosshead 24 and the inner ring 12 of the test bearing housing H. More particularly, and with reference to FIGS. 3, 5 and 6 of the drawings, the lower end of the housing 30 of the friction force scale S' has pivotally connected thereto a depending V-shaped bale 31 that is in turn connected by an S-shaped hook 32 to the horizontally extending portion 33 of a lever arm 34. The lever arm 34 has its inner end 35 fixedly mounted in a projecting annular collar portion 36 of the inner housing ring 12 as more clearly shown in FIG. 6 of the drawings. As shown, the lever arm 34 extends radially outward from the inner ring 12 of the test housing H and is disposed in horizontal position at an angle of 90° to the radial load applied to the housing outer ring 11 by the previously described spring scale S. Normally the lever arm 34 is maintained in this angular relationship with respect to the radially applied load during a bearing test operation of the machine as hereinafter described.

The vertically movable arm 37 of the friction force scale S' has the customary indicating pointer 38 and is connected at its upper end to the lower end of a threaded rod 39. The upper end of the rod 39 projects freely through a bore 40 in the crosshead 24 and has a knurled hand nut 41 threaded thereon in abutting contact with the upper surface of said crosshead 24. As previously described in connection with the adjusting rod 22 of the load scale S, the adjusting rod 39 of the friction force scale S' has a longitudinally extending groove or key way 42 therein that slidably receives a key or pin 43 mounted in the crosshead 24 to thereby prevent rotation of the adjusting rod 39 while permitting adjustable vertical movement thereof.

By reason of the described construction, it will be apparent that by turning the hand nut 41 on the threaded rod 39 in the appropriate direction the vertical upward force or pull exerted by the friction force scale S' on the lever arm 34 can be adjusted according to the friction force generated by rotation of the shaft 7 in the test bearing B to provide an equal counter force and thereby maintain the lever arm 34 at all times in the horizontal position at an angle of 90° with respect to the radial load applied by the load scale S.

In operation of the bearing test machine it occasionally happens that the spring S' may cause the housing inner ring 12 to oscillate and, in order to damp such oscillations should they occur, an adjustable air dashpot 45 is provided in the machine. As shown in FIG. 3 the dashpot 45 is fixedly mounted on the base 1 by means of a bracket 46 so that the dashpot plunger 47 operates in a horizontal direction. The free end of the dashpot plunger 47 is detachably connected, for example, by a slip connector and universal joint arrangement 48, to the lower end of a vertically depending radial lever arm 49 that is mounted in the collar portion 36 of the housing inner ring 12 at an angle of 90° from the lever arm 34 to which the friction force scale S' is connected and diametrically opposite the load applying scale S.

In addition, a stop 51 is mounted on the machine base 1 and positioned in the path of the lever arm 49 to limit rotation of the housing inner sleeve 12 and associated lever arms 34 and 49 and thereby prevent damage to the friction force scale S' and dashpot 45 in the case of abnormal test conditions arising such as generation of excessive friction force or a seized test bearing and the like. In such event, the housing inner ring 12 will be rotated in the clockwise direction with respect to FIG. 3 against the tension of the spring scale S' and engage the lever arm 49 against the stop 51 to prevent further rotation. This will cause a substantial temperature rise as the result of the load on the electric circuit of the motor M thereby activating either or both of the thermal overload protective devices on the starter switch and motor to stop the motor M. Alternatively, a limit stop in the form of a normally closed micro switch (not shown) may be provided in the motor circuit and disposed for engagement by the lever arm 49 to open the circuit of the motor M to stop the latter.

In a typical embodiment of the present invention the spring scale S may be graduated in increments from 0 to 50 lbs. so that by proper adjustment of the thumb nut 25 on the threaded rod 22 a radial load of from 0 to 50 lbs. can be applied to the test bearing B. Similarly, the friction force scale S' may be graduated in both pounds and kilograms; for example, from 0 to 2 lbs. and from 0 to 1kg. which is a range normally adequate for measuring the friction force generated by sliding bearings of the type described under the stated range of loads applied by the load scale S. For ease in reading and data reduction purposes, the kilogram scale is preferred and may be graduated in increments of 0.02 kg. In the illustrated embodiment of the invention the relationship between the active length of the lever arm 34 and the radius of the shaft 7 is such that the actual friction force generated is six times the value indicated on the spring scale S'.

The temperature generated on the shaft by the friction force during a test also may be periodically measured and determined. This may be accomplished by the use of temperature-indicating crayons such as, for example, those available on the market under the registered trade mark "Tempilstiks." Each of these crayons has a calibrated melting point at a specified temperature and are used simply by stroking the rotating shaft from time to time with selected crayons. Below the specified temperature rating the crayon leaves a dry opaque mark on the shaft but when the shaft temperature reaches the rated temperature of the crayon the crayon material melts and leaves a liquid smear on the shaft that is clearly observed.

The machine of the present invention may be used to determine numerous bearing parameters including coefficient of friction, dynamic friction, temperature rise, limiting PV value, wear rate, bearing life and failure mode. The machine may be used to evaluate a single bearing or to evaluate and compare two bearings simultaneously.

To conduct a test, a test bearing is press fitted, for example, into the inner ring 12 of the test bearing housing H which is then mounted on the bearing shaft 7. The load scales S and S' are connected respective to the hook 19 on the housing outer ring 11 and radial lever arm 34 as previously described. Also, the radial lever arm 49 is connected to the dash pot 45.

The hand nut 25 is adjusted to tension the spring scale S to apply a predetermined radial load on the test bearing determined according to the speed of the shaft 7 and the rated PV value of the test bearing. The motor M is then started to drive the shaft 7 at a constant speed within the test bearing and the hand nut 41 is adjusted from time to time as required to tension the spring scale S' and apply to the lever arm 34 a force equal to and opposite the friction force generated by rotation of said shaft and within the test bearing so that said lever arm 34 is maintained in the horizontal position at all times during the test run and the lever arm 49 maintained in the vertical position. At periodic intervals during the test, readings of the generated friction force are obtained from the scale S' and recorded, the coefficient of friction is calculated (either during or after the test) and the temperature generated by friction in the shaft 7 is determined and recorded.

A typical test run is exemplified by the following tabulation of data recorded in a test run of a commercially available lubricant impregnated sintered bronze bearing material claimed to have a PV value of 50,000. The radial load applied was 33 lbs. and the shaft speed was 1725 rpm.

| Time (hrs.) | Temp (° F) | Friction Force | $C_f$ |
| --- | --- | --- | --- |
| 0.0 | 70 | 0.32 | .088 |
| 0.1 | 90 | 0.22 | .068 |
| 0.5 | 120 | 0.17 | .056 |
| 1.0 | 135 | 0.14 | .056 |
| 2.0 | 150 | 0.14 | .056 |
| 3.0 | 150 | 0.14 | .056 |
| 4.0 | 150 | 0.14 | .056 |
| 5.0 | 150 | 0.14 | .056 |
| 10.0 | 150 | 0.14 | .056 |
| 15.0 | 150 | 0.14 | .056 |
| 20.0 | 150 | 0.14 | .056 |
| 25.0 | 160 | 0.16 | .064 |
| 30.0 | 170 | 0.20 | .08 |
| 35.0 | 180 | 0.26 | .10 |
| 40.0 | 190 | 0.30 | .12 |
| 45.0 | 200 | 0.34 | .14 |
| 48.0 | 220 | 0.40 | .16 |

| Time (hrs.) | Temp (° F) | Friction Force | $C_f$ |
|---|---|---|---|
| 49.1 | 300 | 1.00 | .36 |

In the foregoing test, the PV rating of 50,000 claimed for the test bearing indicated the application of a radial load on the test bearing of about 54 lbs. However, the test engineer considered such a load too high and selected the lesser load of 33 lbs. Even under the load of 33 lbs. the test bearing failed after 49.1 hours operation as indicated by the temperature and friction force which rose so high that the protective thermal overload functioned to stop the motor M and shut down the machine. In the foregoing tabulation it will be noted that the temperature and friction force became relatively stabilized after 1 hour and remained so until after 20 hours when the temperature and friction force commenced to increase until the failure point at 49.1 hours.

The test established that the 50,000 PV value claimed for the test bearing was incorrect and exaggerated as was a PV value of 30,000 at the selected test load of 33 lbs. It was later determined that the correct PV value for the test bearing was about 18,000 and that under a proper radial load of about 20 lbs. the test bearing could be expected to provide a normal operating life of about 2000 hours.

From the foregoing it will be apparent that the present invention provides a machine that can be used effectively to perform numerous functional and comparative tests on radially loaded sliding bearings, including endurance and life tests at predetermined PV values, and the measurement and determination of the dynamic coefficient of friction of such bearings under any given load and speed at all times during the test period.

While a typical embodiment of the invention has been shown and described, it is not intended to limit the invention to such disclosure, and the invention is intended to cover any and all bearing test machines coming within the scope of the following claims.

We claim:

1. In a machine for testing and comparing sliding bearings,
   an annular test bearing housing comprising radially spaced concentric outer and inner rings, said inner ring having an internal diameter dimensioned to receive and fixedly retain therein a selected test bearing,
   bearing means intermediate the outer and inner rings rotatably supporting said rings relative to each other,
   a rotatable shaft dimensioned for coaxially mounting thereon the selected test bearing secured in the inner ring of said housing,
   means operable to rotationally drive said shaft at a selected constant speed,
   test bearing loading means connected to the housing outer ring arranged and adjustably operable to apply a predetermined load radially on the test bearing secured in the inner ring of said housing,
   a lever arm secured to an extending radially outward from the inner ring of the housing adapted to be disposed at an angle of 90° from said radially applied load,
   and friction force measuring means connected to said lever arm arranged and adjustably operable to exert thereon a counter force equal to the friction force generated by rotation of the shaft in the test bearing and thereby maintain the lever arm disposed at said angle of 90° from the radial load,
   said friction force measuring means including means indicating the amount of said counter force and thereby the amount of the generated friction force.

2. A machine as claimed in claim 1 wherein the test bearing loading means comprises a spring scale including a spring operable to exert a radial tension force on the housing outer ring and the test bearing, and means selectively operable to adjustably vary the tension force of said spring and thereby the radial load applied to the test bearing.

3. A machine as claimed in claim 1 wherein the friction force measuring means comprises a spring scale including a spring operable to exert a tension force on the lever arm connected to the housing inner ring, and means selectively operable to adjustably vary the tension force of said spring and provide a counter force on said lever arm equal to the friction force generated by rotation of the shaft in the test bearing.

4. A machine as claimed in claim 2 wherein the friction force measuring means comprises a spring scale including a spring operable to exert a tension force on the lever arm connected to the housing inner ring, and means selectively operable to adjustably vary the tension force of said spring and provide a counter force on said lever arm equal to the friction force generated by rotation of the shaft in the test bearing.

5. A machine as claimed in claim 1 comprising a second lever arm secured to and extending radially outward from the housing inner ring at an angle of 90° from the first mentioned lever arm and diametrically opposite the test bearing loading means, and a dashpot operable normal to said second lever arm and connected to the outer end thereof for damping any oscillations imparted to the housing inner ring.

6. A machine as claimed in claim 1 comprising stop means operable to predeterminedly limit rotation of the housing inner ring and lever arm relative to the friction force measuring means.

7. A machine as claimed in claim 6 comprising means responsive to limited rotation of the housing inner ring and lever arm as determined by the stop means operable to stop the shaft drive means.

8. A machine as claimed in claim 5 comprising stop means disposed in the path of the second lever arm and engageable thereby to predeterminedly limit rotation of the housing inner ring and first mentioned lever arm relative to the friction force measuring means.

9. A machine as claimed in claim 8 comprising means responsive to limited rotation of the housing inner ring and lever arm as determined by the stop means operable to stop the shaft drive means.

10. A machine as claimed in claim 3 comprising a second lever arm secured to and extending radially outward from the housing inner ring at an angle of 90° from the first mentioned lever arm and diametrically opposite the test bearing loading means, and a dashpot operable normal to said second lever arm and connected to the outer end thereof for damping any oscillations imparted to the housing inner ring.

11. A machine as claimed in claim 3 comprising, stop means operable to predeterminedly limit rotation of the housing inner ring and lever arm relative to the friction force measuring means.

12. A machine as claimed in claim 10 comprising stop means disposed in the path of the second lever arm and engageable thereby to predeterminedly limit rotation of the housing inner ring and first mentioned lever arm relative to the friction force measuring means.

13. In a machine for testing and comparing sliding bearings, a pair of laterally spaced bearing test stations each including an annular test bearing housing comprising radially spaced concentric outer and inner rings, said inner ring having an internal diameter dimensioned to receive and fixedly retain therein a selected test bearing, bearing means intermediate the outer and inner rings of each housing rotatably supporting said rings relative to each other, a rotatable shaft in each test station dimensioned for coaxially mounting thereon the selected test bearing secured in the inner ring of the test housing in said station, means operable to rotationally drive each of said shafts at the same selected constant speed, test bearing loading means connected to the outer ring of each housing arranged and adjustably operable to apply a predetermined load radially upon the test bearing in said housing, a lever arm secured to and extending radially outward from the inner ring of each housing adapted to be disposed and maintained at an angle of 90° from said radially applied load, and friction force measuring means connected to each lever arm arranged and adjustably operable to exert thereon a counter force equal to the friction force generated by rotation of the shaft in the test bearing and thereby maintain the lever arm disposed at said angle of 90° from the radial load, each said friction force measuring means including means indicating the amount of said counter force and thereby the amount of the generated friction force.

14. A machine as claimed in claim 13 wherein each test bearing loading means comprises a spring scale including a spring operable to exert a radial tension force on the associated housing outer ring and the test bearing, and means selectively operable to adjustably vary the tension force of said spring and thereby the radial load applied to the test bearing.

15. A machine as claimed in claim 13 wherein each friction force measuring means comprises a spring scale including a spring operable to exert a tension force on the lever arm connected to the associated housing inner ring and means selectively operable to adjustably vary the tension force of said spring and provide a counter force on said lever arm equal to the friction force generated by rotation of the shaft in the test bearing.

16. A machine as claimed in claim 14 wherein the friction force measuring means comprises a spring scale including a spring operable to exert a tension force on the lever arm connected to the associated housing inner ring, and means selectively operable to adjustably vary the tension force of said spring and provide a counter force on said lever arm equal to the friction force generated by rotation of the shaft in the test bearing.

17. A machine as claimed in claim 13 comprising a second lever arm secured to and extending radially outward from each housing inner ring at an angle of 90° from the first mentioned lever arm and diametrically opposite the test bearing loading means, and a dashpot operable normal to said second lever arm and connected to the outer end thereof for damping any oscillations imparted to the housing inner ring.

18. A machine as claimed in claim 17 comprising stop means disposed in the path of each second lever arm and engageable thereby to predeterminedly limit rotation of the housing inner ring and first mentioned lever arm relative to the friction force measuring means.

19. A machine as claimed in claim 18 comprising means responsive to limited rotation of the housing inner ring and lever arm as determined by the stop means operable to stop the shaft drive means.

20. A machine as claimed in claim 16 comprising a second lever arm secured to and extending radially outward from each housing inner ring at an angle of 90° from the first mentioned lever arm and diametrically opposite the test bearing loading means, and a dashpot operable normal to said second lever arm and connected to the outer end thereof for damping any oscillations imparted to the housing inner ring.

21. A machine as claimed in claim 20 comprising stop means disposed in the path of each second lever arm and engageable thereby to predeterminedly limit rotation of the housing inner ring and first mentioned lever arm relative to the friction force measuring means.

22. A machine as claimed in claim 21 comprising means responsive to limited rotation of the housing inner ring and lever arm as determined by the stop means operable to stop the shaft drive means.

* * * * *